United States Patent [19]
Taylor

[11] Patent Number: 5,911,727
[45] Date of Patent: Jun. 15, 1999

[54] STITCHER

[75] Inventor: Charles Taylor, San Francisco, Calif.

[73] Assignee: Cardiothoracic Systems, Inc., Cupertino, Calif.

[21] Appl. No.: 08/791,457

[22] Filed: Jan. 27, 1997

Related U.S. Application Data

[63] Continuation-in-part of application No. 08/650,153, Feb. 20, 1996.

[51] Int. Cl.$^6$ ........................................ A61B 17/04
[52] U.S. Cl. ........................ 606/145; 606/144; 606/145; 606/139
[58] Field of Search ..................... 606/144, 145, 606/139, 148; 112/169

[56] References Cited

U.S. PATENT DOCUMENTS

| | | |
|---|---|---|
| 1,822,330 | 9/1931 | Ainslie . |
| 4,027,608 | 6/1977 | Arbuckle . |
| 4,109,658 | 8/1978 | Hughes . |
| 4,235,177 | 11/1980 | Arbuckle . |
| 4,345,601 | 8/1982 | Fukuda . |
| 4,557,265 | 12/1985 | Andersson . |
| 4,899,746 | 2/1990 | Brunk . |
| 5,306,281 | 4/1994 | Beurrier . |
| 5,308,353 | 5/1994 | Beurrier . |
| 5,437,681 | 8/1995 | Meade et al. . |

*Primary Examiner*—Michael Buiz
*Assistant Examiner*—Tina T. D. Pham
*Attorney, Agent, or Firm*—Lyon & Lyon LLP

[57] ABSTRACT

An automated stitching device having a "C"-shaped arcuate needle which is incrementally advanced in a circular path. A toggle and drive plate arrangement is used to drive the needle, and a one-way clutch mechanism is used to engage and permit incremental advancement of the needle along its circular path. The "C"-shaped arcuate needle is mounted and driven at the distal end of an elongated shaft. The stitching device is particularly suited for microsurgery, laparoscopic surgery, and various less invasive surgical procedures, and particularly for the suturing of blood vessels including during cardiac bypass surgery.

3 Claims, 7 Drawing Sheets

STITCHER

This application is a continuation-in-part of Ser. No. 08/650153, filed Feb. 20, 1996.

FIELD OF THE INVENTION

This invention relates generally to an automated stitching or suturing device. More particularly, this invention relates to an automated stitching or suturing device which can be used advantageously in surgical procedures such as coronary artery bypass grafting (CABG) surgery, laparoscopic procedures, and various less invasive surgical procedures.

BACKGROUND OF THE INVENTION

Suturing by surgeons is currently generally accomplished by manual suturing of tissues, whereby the surgeon uses a fine pair of pliers to grab and hold a suture needle, pierce the tissue with the needle, let go of the needle, and regrab the needle to pull the needle and accompanying suture thread through the tissues to be sutured. Such needles may be curved or "C"-shaped, with the suture thread attached to the back end of the needle.

Automated suturing devices, including devices described as suitable for microsurgery, are known. For example, U.S. Pat. No. 4,557,265 to Andersson describes a suturing instrument for joining two edges of biological tissue, such as blood vessels, using an arcuate suture needle which is driven and rotated by friction rollers via a cylindrical fly-wheel and plunger rod arrangement with a pneumatic or other drive source, so that the suture thread forms a continuous suture looped through the two tissue edges. U.S. Pat. No. 4,899,746 to Brunk describes a suturing apparatus in which an electric motor drives a curved needle around in a circular path of travel by means of a gear arrangement connecting to a plurality of drive rollers in supporting and driving arrangement with the needle. U.S. Pat. No. 5,308,353 to Beurrier describes a surgical suturing device in which an arcuate needle having outward projecting angled barbs positively engages and is rotated by a continuous loop drive belt.

However, such known automated suturing devices have not found wide use due to the inherent deficiencies of their design and operation, including needle slippage, inefficient transfer of drive motion to the advancement of the needle, inefficient and impractical drive mechanisms, and generally poor performance of the devices, particularly for microsurgical applications where a very small size for the device is required. Accordingly, there is a need for an improved suturing device which overcomes these deficiencies.

SUMMARY OF THE INVENTION

The stitcher device of the present invention is an automated stitching or suturing device in which a "C"-shaped arcuate suturing needle is positively driven in a circular path to suture tissues, including blood vessels. The "C"-shaped arcuate needle is held and advanced in increments by clutches and by a drive plate and toggle mechanism, which converts rotary motion to oscillating motion, and is powered via a drive shaft connected to an electric motor. The "C"-shaped needle and drive plate are positioned at the end of an elongated shaft. The stitcher is particularly adapted for use in microsurgery and/or in interior body spaces. For example, in coronary bypass surgery, the stitcher device of the present invention is able to precisely and rapidly place stitches to join grafts to coronary arteries and to seal leaks in the grafted vessels.

In general, it is an object of the present invention to provide an automated stitcher device which can be used for surgical and other applications. A further object of the invention is to provide a suturing instrument which can be used for microsurgical applications, including the suturing of blood vessels, and preferably which can be operated by a surgeon using one hand.

Additional objects and features of the invention will appear from the following description in which preferred embodiments are set forth in detail in conjunction with the accompanying drawings.

DETAILED DESCRIPTION OF THE INVENTION

Figure 1:
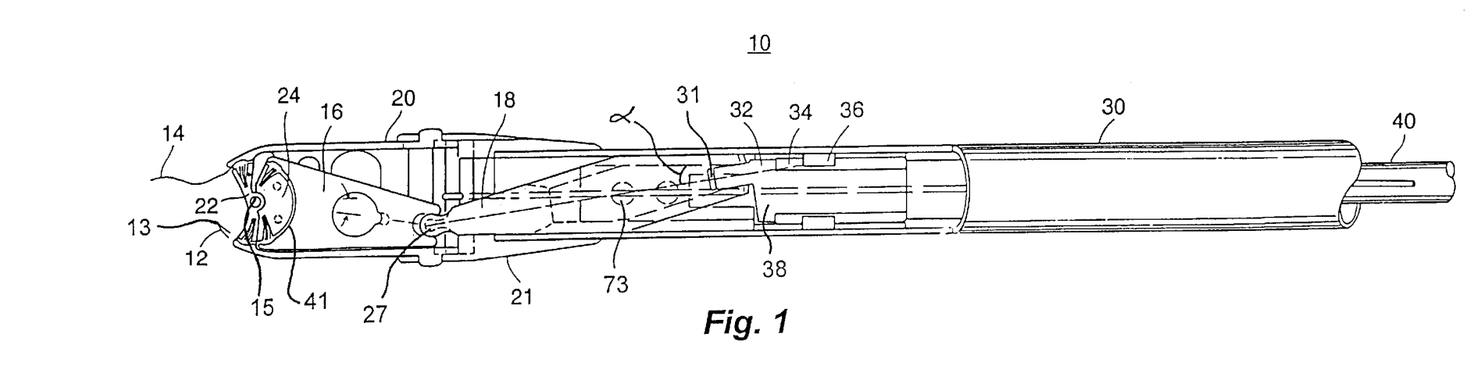
FIG. 1 is a cut-away top view of the distal portion of one embodiment of the stitcher.
Figures 4, 5:
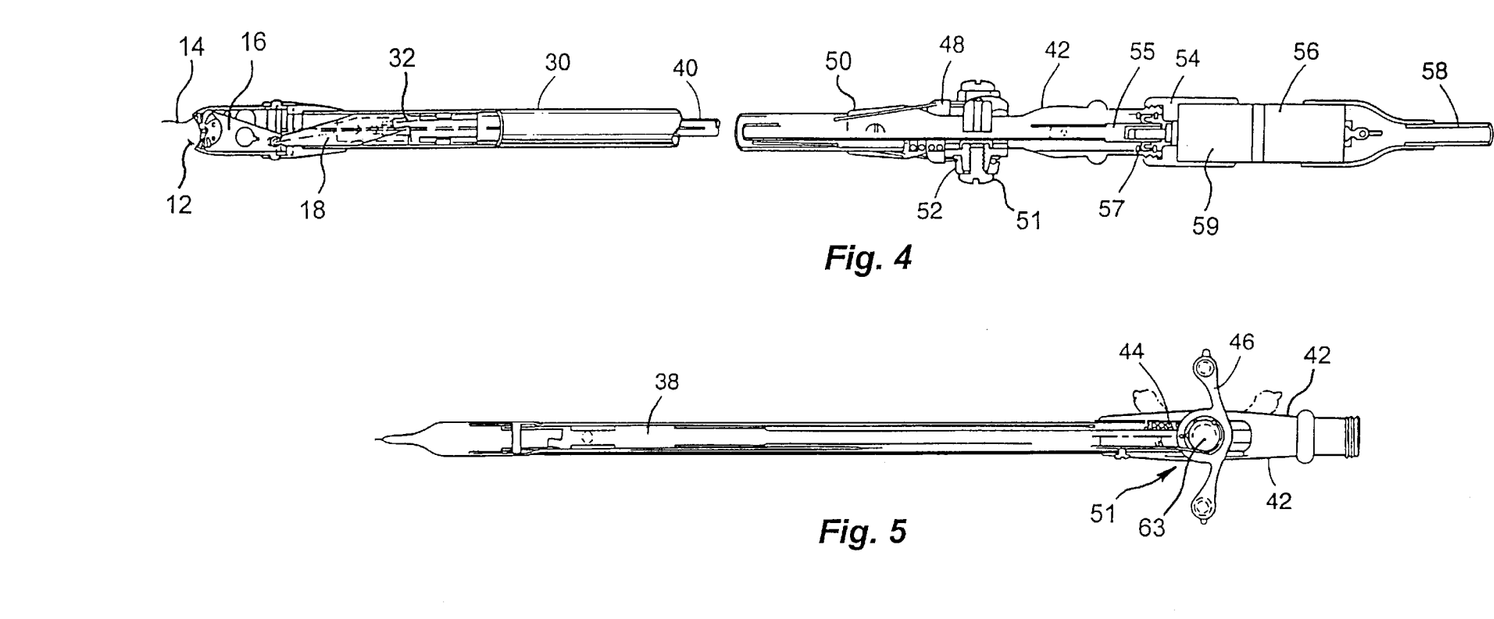
FIG. 4 is a cut-away top view of the full length of the stitcher.
FIG. 5 is a side view of the main portion of FIG. 4.
Figure 6:
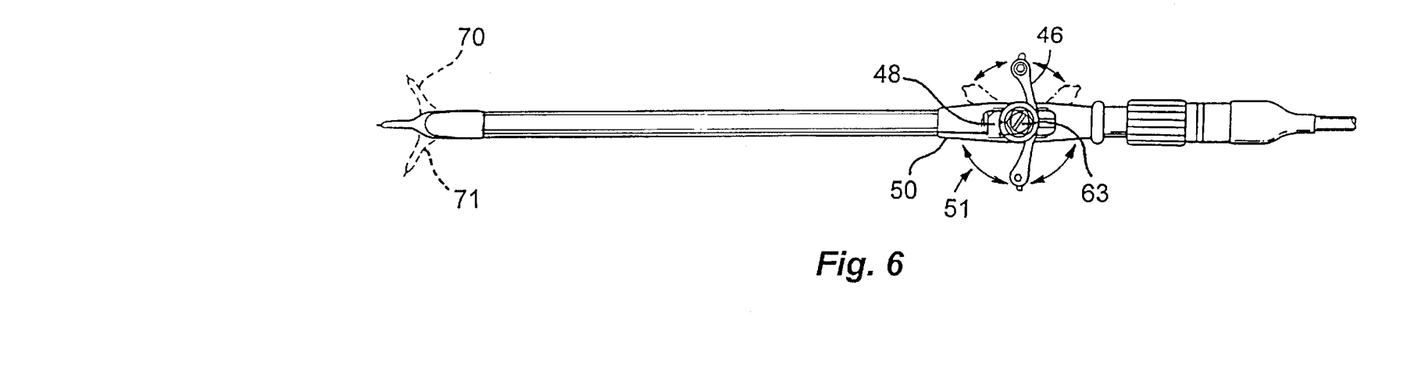
FIG. 6 is a side view of FIG. 4 showing three positions for the stitcher distal nose tip.

Turning in detail to the drawings, with like reference numbers referencing like components, FIG. 1 shows the distal portion of a stitcher 10 incorporating a preferred embodiment of the present invention generally comprising an elongated tubular body or housing member 30, a head assembly 21, and a nose tip 20 having a "C"-shaped arcuate needle 12 slidably mounted therein for 360° rotation within nose tip 20. Housed within head assembly 21 and tubular body 30, from the distal end or nose tip 20 to the proximal end, are a drive plate 16, a diamond-shaped toggle 18, a crank pin 32, crank shaft 38, drive shaft 40 (FIGS. 1 and 2), and a nose tip articulation mechanism 51 (FIGS. 4–6). At the proximal end of stitcher 10 is an electric motor 56 coupled to the stitcher base 42 (FIG. 4).

Stitcher 10 is preferably made of medical grade stainless steel, and is designed to be held in the hand, similar to the way a pencil or pen is held. The length of stitcher 10 from nose tip 20 to stitcher base 42 is approximately between 15 and 20 cm but may be more or less depending on the application. Tubular housing 30 has a diameter more or less equal to the diameter of the arc of needle 12. Preferably, the length and diameter of stitcher 10 are configured for use in conventional open surgeries as well as minimally invasive surgeries.

Figure 1A:
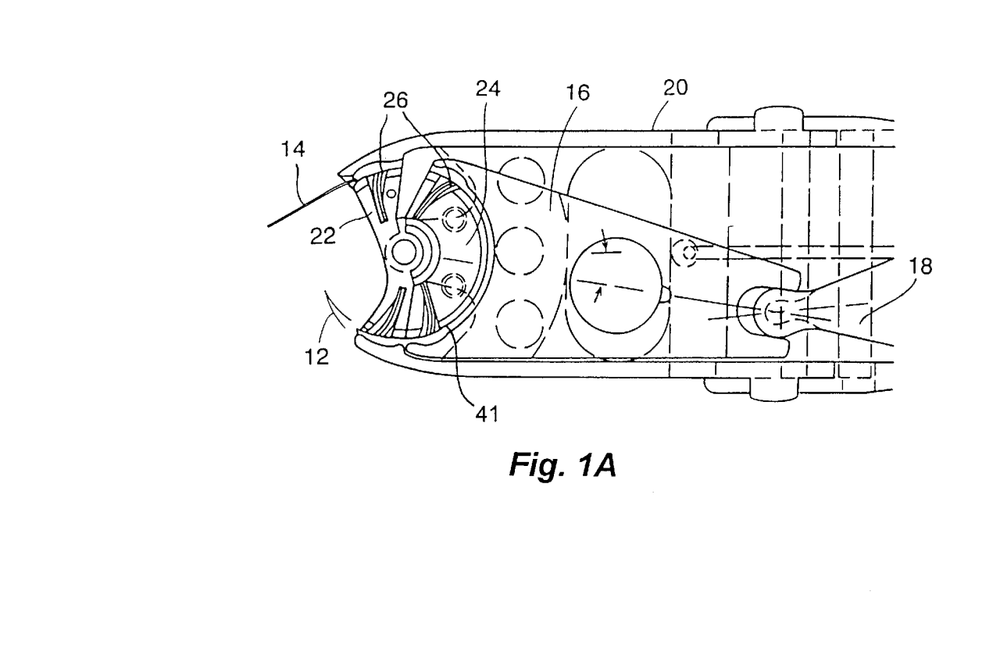
FIG. 1A is an enlarged view of the distal extremity of FIG. 1.
Figure 7:
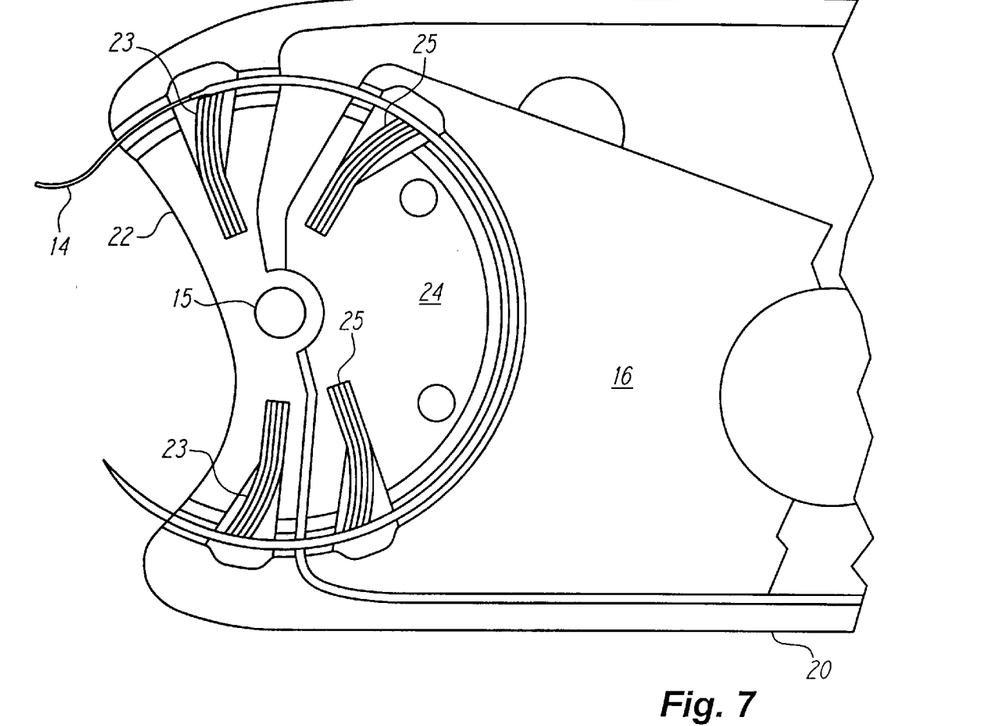
FIG. 7 is an enlarged cut-away top view of the embodiment of the nose tip of the stitcher in FIGS. 1 and 1A.

As is more clearly shown in FIGS. 1A and 7, needle 12 has an arc preferably in the range between about 200° and 300°, and more preferably has an arc about 270°. Needle 12 has a sharp point 13 at one end and a suturing thread 14 attached to the other end thereof. The diameter of needle 12 is approximately 0.23 mm (0.011 inches), a typical diameter for surgical needles, and the outer diameter of the arc of needle 12 is preferably about 6–7 mm (0.25 inches). Needle 12 is preferably made of stainless steel; however, other surgical grade materials are suitable, as will be appreciated by those skilled in the art.

Needle 12 is engaged and held at nose tip 20 within an arcuate guide, track, groove, or channel 41 which extends around an arc of more than about 180° and has the same radius of curvature as needle 12. Arcuate guide 41 is defined by a static guide or clutch body 22 and also by a dynamic guide or clutch body 24, as well as by a drive plate 16. Because needle 12 extends along an arc greater than 180°, at least a portion of needle 12 is always in positive engagement within guide 41. During operation of stitcher 10, needle 12 is caused to travel about guide 41 by actuation of dynamic clutch body 24, about rivet 15. The function of static and dynamic clutch bodies 22 and 24 is described in more detail below.

Static clutch body 22 has one or more clutch components or engaging units 23, and dynamic clutch body 24 has one or more clutch components or engaging units 25. Each clutch component 23, 25 is comprised of a plurality of clutch fingers 26 extending radially outward at a slight arc from clutch bodies 22 and 24 which engage the inner curved surface of the needle 12. For example, the clutch component may be composed of a stack or fan configuration of bendable or flexible leaf springs or reeds, each having a length of about 2 mm (0.07 inches) and a width of about 0.5 mm (0.02 inches). These fingers 26 are preferably made of hardenable 17-7 stainless steel. Although static clutch body 22 and dynamic clutch body 24, as shown in FIGS. 1, 1A, and 7, each have two clutch components 23, 25 each having four clutch fingers 26, more or fewer clutch components and/or fingers may be used for each clutch body. For example, dynamic clutch body 24 may have multiple engaging units spaced along its arcuate guide 41 an arcuate distance preferably greater than about 90°. Additionally, solid sprags could be used in place of the flexible clutch fingers.

Figure 7A:
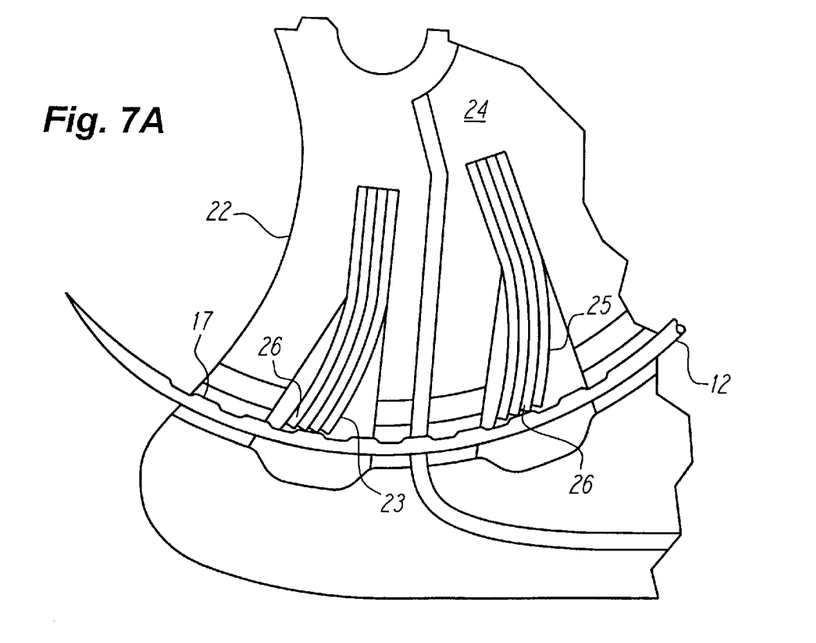
FIG. 7A is a further enlargement of a portion of FIG. 7 depicting engagement of a needle with the clutch components of the stitcher.

In a preferred embodiment, as shown in FIG. 7A, needle 12 has a series of radially inward projecting protuberances or protrusions 17 on its inner curved surface for engaging one or more clutch components or engaging units 23 of static clutch body 22 and one or more clutch components or engaging units 25 of dynamic clutch body 24. More specifically, protuberances 17 and clutch components 23, 25 are designed and have dimensions which allow a clutch component to frictionally engage the needle within the valleys or spaces between the protuberances. The peak-to-peak distance of the protuberances is approximately 0.20 to 0.25 mm and preferably about 0.22 mm (0.0087 inches), and the height of protuberances 17 from the inner diameter of needle 12 to the peak of protuberances 17 is approximately 0.03 to 0.05 mm and preferably about 0.04 mm (0.0015 inches).

Figure 2:
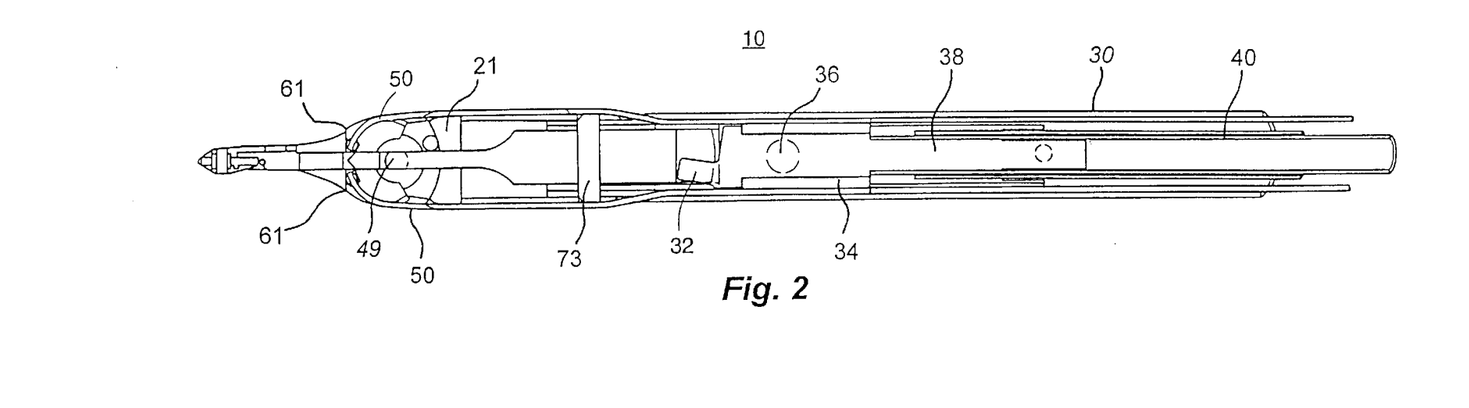
FIG. 2 is a side view in cross-section of FIG. 1.

The operation of stitcher 10 is as follows. A crank shaft 38 is driven by the rotational movement of elongated drive tube shaft 40 which is, in a preferred embodiment, powered by electric motor 56 (see FIG. 4). Motor 56 is of a type commonly known, for example having a gear head 59 which rotates drive shaft 40 when motor 56 is operably coupled to a power supply (not shown) via associated electric cable 58. Alternately, a pneumatic or hand-driven, rather than an electric, motor drive could be used. Crank shaft 38 and drive shaft 40 are coaxially provided and rotationally moveable within a bearing sleeve 34 (FIG. 2). Bearing sleeve 34 is fixed to tubular housing 30 by means of keys 36, and allow crank shaft 38 and drive shaft 40 to rotate independently of tubular body 30.

As can be seen in FIG. 1, crank shaft 38 has a crank pin 32 extending from its distal end at an acute angle α from the longitudinal axis of crank shaft 38, and resides within a slot 31 that extends through the diameter in the proximal end of a diamond-shaped toggle 18. A pin 73 extends through the longitudinal center of toggle 18 and serves to maintain alignment of the toggle 18 as well as crank shaft 38 and drive shaft 40 within tubular housing 30. In order for crank pin 32 to maintain continuous alignment within slot 31 as crank shaft 38 rotates, angle α is such that the longitudinal axis of crank pin 32 passes through the center of pin 73. Accordingly, α is between about 5° and 10°, and closer to 7°.

FIG. 2 provides a side cross-sectional view of the distal portion of the stitcher 10, showing the crank pin 32 and its engagement with toggle 18, wherein crank pin 32 has been rotated and toggle 18 has been oscillated 90° from their respective positions in FIG. 1. The distal end of toggle 18 tapers to a spherically shaped tip 27 which mates with the slotted configuration of the proximal end of drive plate 16.

The crank-toggle configuration described converts the rotary motion of drive shaft 40 and crank shaft 38 to the oscillating motion of toggle 18, which, in turn, moves drive plate 16 back and forth (which is up and down as viewed in FIG. 1). In addition, alternate crank-toggle configurations, such as that depicted in FIGS. 8–10, may also be used to effect the translation of rotary to oscillating motion.

Figure 8:
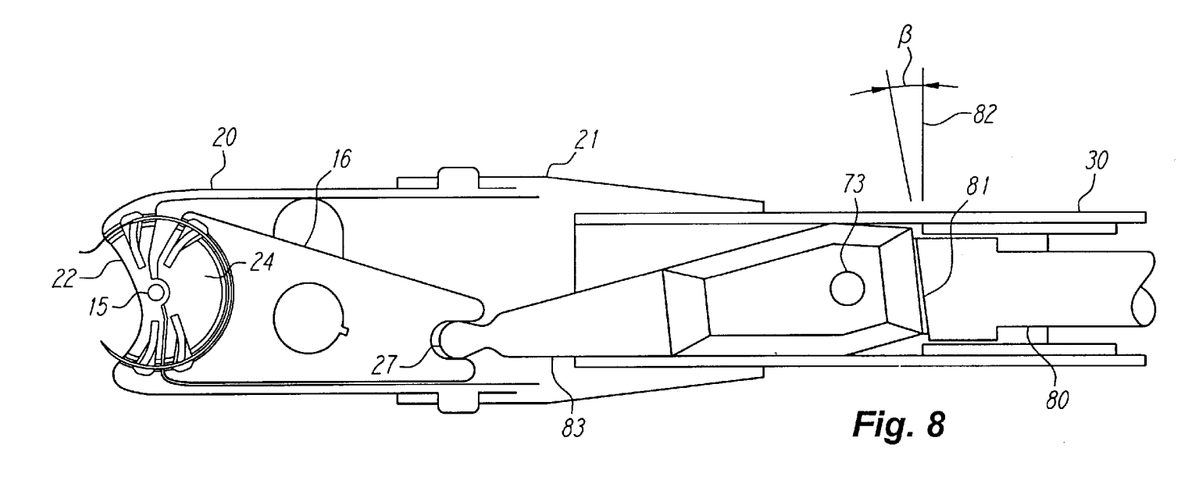
FIG. 8 is a cut-away top view of the distal portion of another embodiment of the stitcher.
Figure 9:
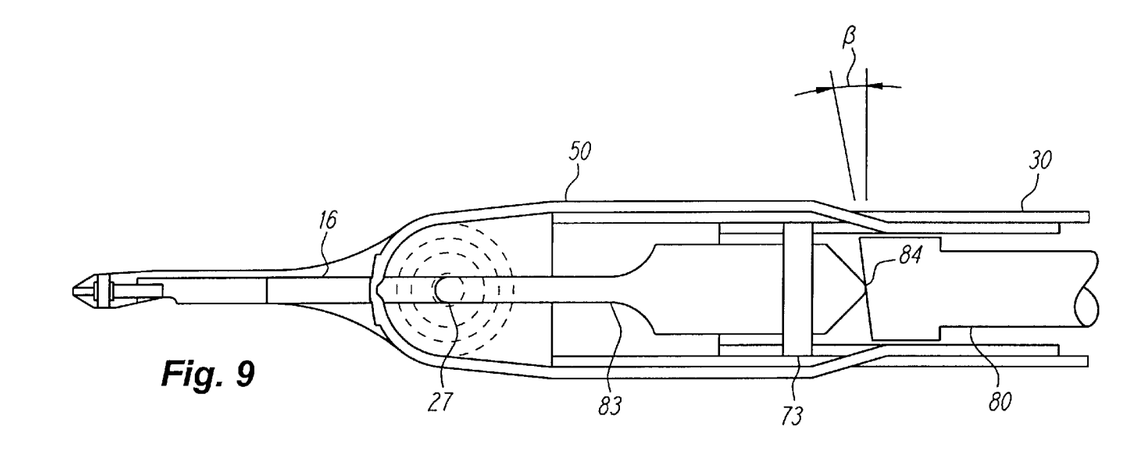
FIG. 9 is a side view in cross-section of FIG. 8.
Figure 10:
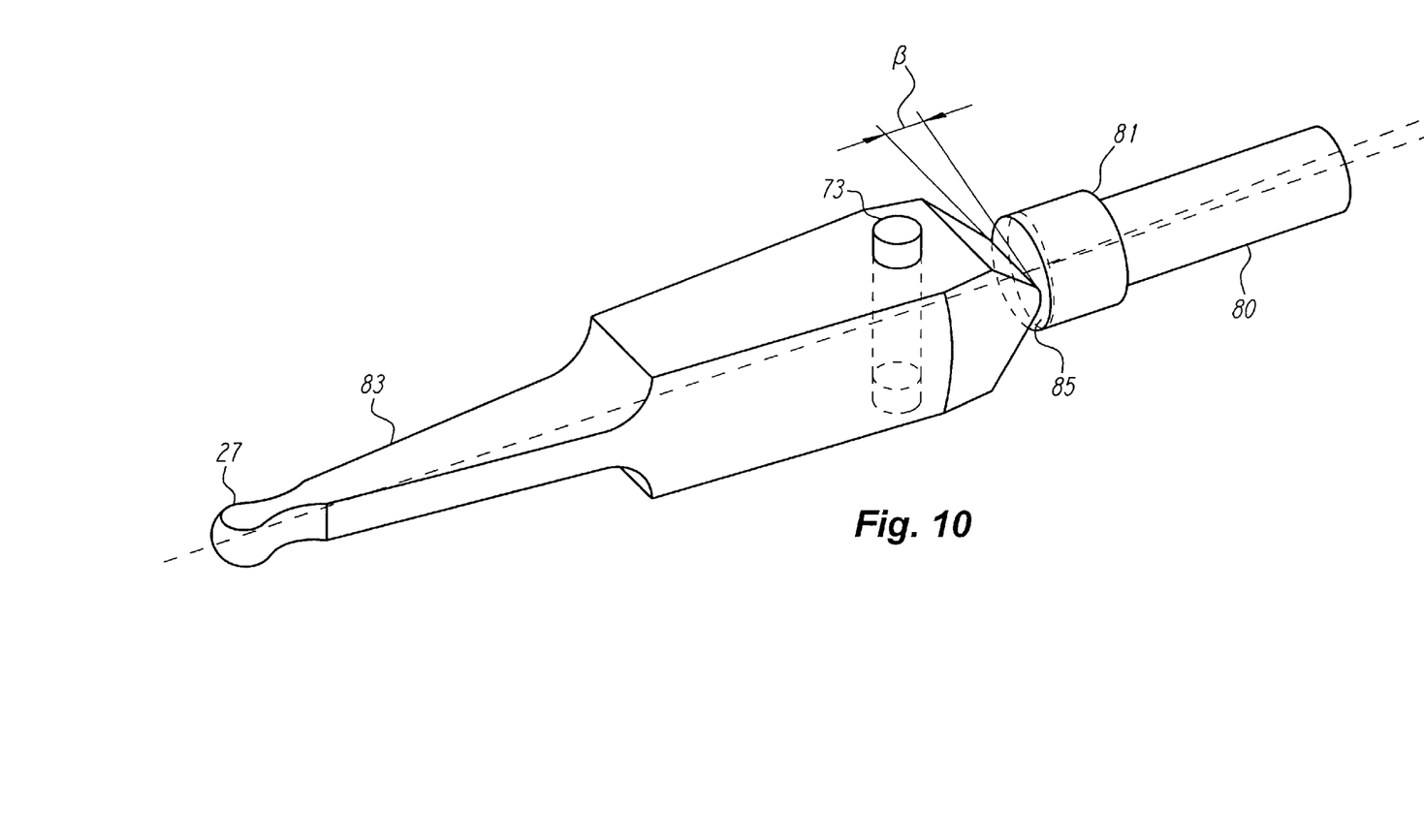
FIG. 10 a perspective view of the crank-toggle configuration of the embodiment of FIGS. 8 and 9.

FIGS. 8 and 9 illustrate cut-away views of the distal portion of a stitcher having a crank shaft 80 with a distal end in the form of a swash plate 81. The face 85 of swash plate 81 extends forward at a slight angle β from the vertical axis 82 and abuts toggle 83 at its proximal end 84, which is in the form of a triangular wedge, as is more clearly seen in FIG. 10. Angle β is such that face 85 is perpendicular to the central axis of toggle 83 when proximal end 84 is in its extreme positions. Here, β is between about 5° and 10°, and closer to 7°. FIG. 9 shows a cross-sectional side view of crank shaft 80 and toggle 83 when toggle 83 is in a centered position, or otherwise described as half-way between its extreme positions.

Referring again to FIGS. 1, 1A, 2A, and 7, at the distal end of drive plate 16 is formed the dynamic clutch body 24. The oscillating movement of drive plate 16 rocks the dynamic clutch body 24 back and forth in an arcuate path, which incrementally and non-continuously advances the arcuate needle 12 in a circular path within guide 41 and about an axis, defined by a rivet 15, which is perpendicular to the longitudinal axis of tubular housing 30. Needle 12 is advanced in less than about 180° increments, and preferably less than about 30° increments, and more preferably about 15° increments.

In a preferred embodiment, clutch bodies 22, 24 are one-way or uni-directional clutches. As shown in FIG. 7, the sets of clutch fingers 26 are slightly arced in the direction that needle 12 is advanced, here, in a clockwise direction.

Each set of clutch fingers 26 occupies at least a substantial portion of the space between two consecutive protuberances 17. When dynamic clutch body 24 is caused to rotate in the clockwise direction, its associated clutch components 25 grip needle 12 and advance it in the clockwise direction. However, when dynamic clutch body 24 is caused to rotate in the counter-clockwise direction (opposite the direction in which fingers 26 are pointing), the flexible arced clutch components 25 are able to freely slide over protuberances and, thus, release needle 12. Simultaneously, arced clutch components 23 of static clutch body 22 grip and hold needle 12, and ensure that needle 12 is held in place until the next incremental, clockwise advancement of dynamic clutch body 24 by drive plate 16. The slight forward arcing of clutch fingers 26 prevents needle 12 from sliding backwards or in the counter-clockwise direction when dynamic clutch body 24 is rotated in a forward or clockwise direction. In another embodiment, clutch fingers 26 may be arced in a counter-clockwise direction which would act to advance needle 12 in a counterclockwise direction upon the oscillation of drive plate 16 and dynamic clutch body 24.

In other embodiments, the inner curved surface of the needle 12 may be smooth or roughened, or contain gears, ratchet teeth, or like protrusions to aid in gripping of the clutch elements, or the clutch bodies 22, 24, may be bi-directional clutches.

Other clutch mechanisms may also be utilized with the stitcher of the present invention to hold and facilitate incremental advancement of arcuate needle 12 by drive plate 16. For example, one-way bearings or rollers may be used, positioned along the inner curved side (FIG. 11) or the outer curved side (FIG. 12) of arcuate needle 12, and such bearings or roller clutches serve to engage, hold, or secure the needle while permitting its incremental advancement.

Figure 11:
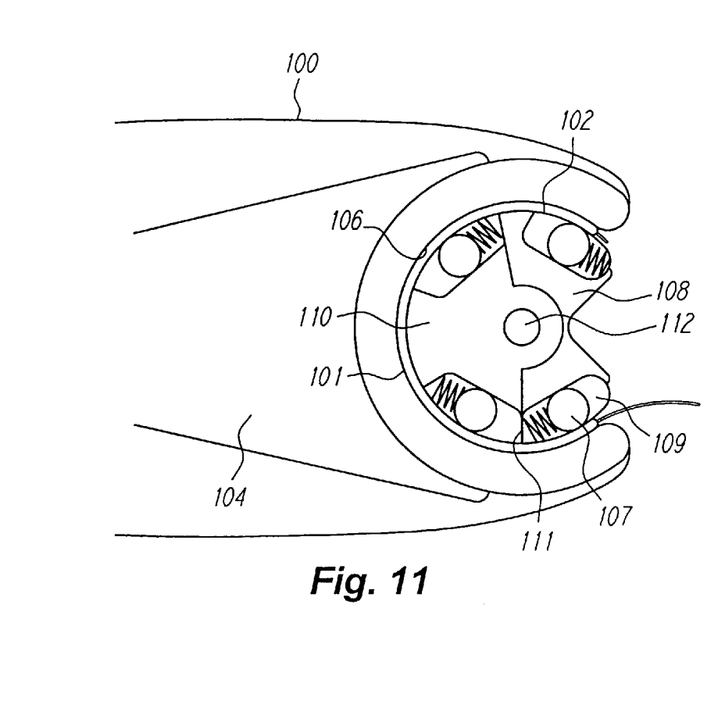
FIG. 11 is a cut-away portion of another embodiment of the nose tip and clutch components of the stitcher.
Figure 12:
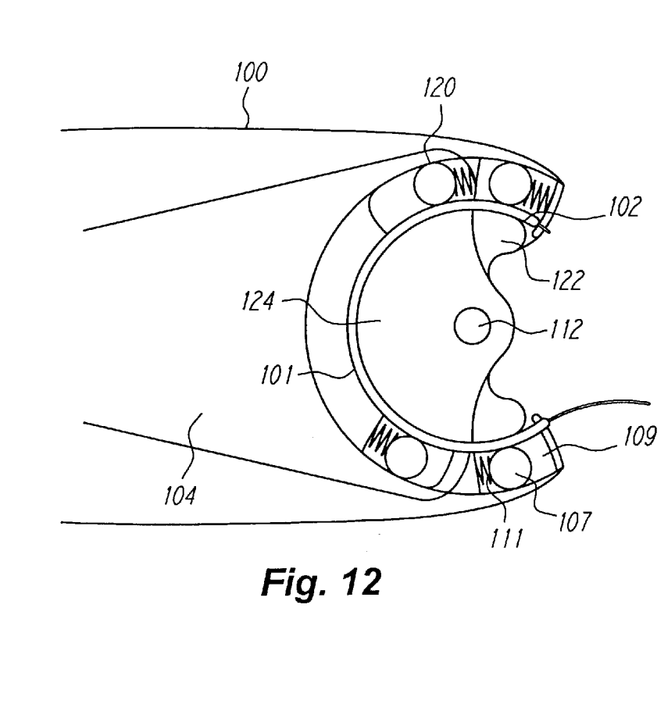
FIG. 12 is a cut-away portion of another embodiment of the nose tip and clutch components of the stitcher.

FIGS. 11 and 12 show cut-away portions of the nose tip 100 of a stitcher having a needle 102 held within a channel 101 defined by respective static and dynamic clutch bodies and drive plates 104. The roller or bearing clutches 106 of FIG. 11, two associated with each of static clutch body 108 and dynamic clutch body 110, are positioned on the inside curved side of needle 102. In FIG. 12, the roller or bearing clutches 120, two associated with static clutch body 122 and dynamic clutch body 124, respectively, are positioned on the outside curved side of needle 102. As with embodiments discussed previously, the dynamic clutch bodies of the embodiments of FIGS. 11 and 12 are integral with their respective drive plates 104 and rotate about a rivet 112 when the drive plate 104 is rotated, while static clutch body 108 remains in a fixed position.

Each roller clutch 106 (FIG. 11) and 120 (FIG. 12) comprises a roller or bearing 107 which resides within a curved bearing slot having a tapered rearward section 109 and a forward section occupied by a spring 111 which is biased against bearing 107. The width of tapered rearward section 109 is less than the diameter of bearing 107 such that the spring bias causes bearing 107 to be frictionally engaged within rearward section 109. Accordingly, when drive plate 104 and dynamic clutch body 110 of FIG. 11 are rotated in a forward or clockwise direction, bearings 107 of both the dynamic and static clutch bodies 110 and 108 are caused to sufficiently overcome the spring bias and roll clockwise, allowing needle 102 to advance in a forward or clockwise direction within channel 101. However, when dynamic clutch body 110 is caused to rotate in a backward or counter-clockwise direction, bearings 107 of FIG. 11 are, in turn, caused to become frictionally engaged within tapered end 109 of the bearing slot and are unable to roll. The bearings 107 of static clutch body 108 exert a sufficient force on needle 112 to hold it in its advanced position while dynamic clutch body 110 is rotated backward or counter-clockwise. The bearing 107 of dynamic clutch body 110 slide along needle 112 but do not overcome the force exerted on needle 112 by the now static bearings of static clutch body 108. In this way, needle 112 can be incrementally advanced in an arcuate path. The operation of static and dynamic clutch bodies 122 and 124 of FIG. 12 is similar to that of FIG. 11 with the exception that bearings 107 of roller clutches 120 roll counter-clockwise when dynamic clutch body 124 is rotated in a forward or clockwise direction.

With the various embodiments of the present invention, the sequential steps of gripping, incrementally advancing, and then releasing of a surgical needle by the dynamic clutch body are repeated as needed for driving the needle to form the desired suture.

Figure 2A:
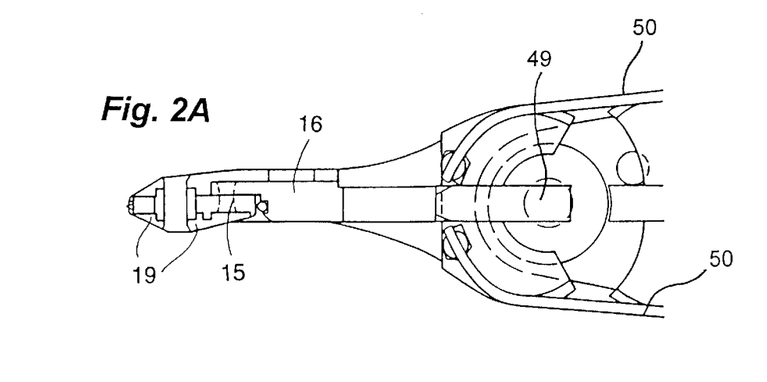
FIG. 2A is an enlarged view of the distal extremity of FIG. 2.
Figure 3:
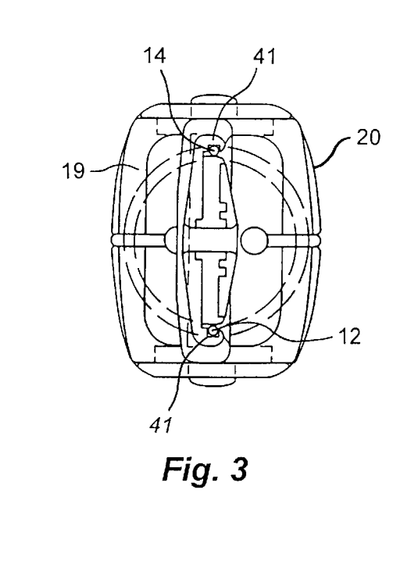
FIG. 3 is a cross-sectional end view of the distal nose tip of the stitcher.

Returning to a description of the other stitcher components, FIGS. 1A, 2A, and 3 show the details of nose tip 20 at the distal extremity of stitcher 10. FIG. 2A shows a circular assembly cap plate 19 with a rivet 15 at stitcher nose tip 20. Cap plate 19 serves to hold in place and cover static clutch body 22 and dynamic clutch body 24 to prevent blood, tissue particles, dust, and other undesirable elements from interfering with these components.

As shown in FIGS. 1A and 3, thread 14, being attached to the back end of the needle 12, will follow the rotation of the needle 12, but may be offset from the path of the needle 12. As discussed above, the components of the nose tip 20 may form an arcuate guide or a circular groove or track 41 within which the arcuate needle 12 is disposed.

FIG. 4 provides a view of the full length (with a cut-away section) of stitcher 10, having motor 56 with gear head 59 coupled to the stitcher base 42 by means of threaded motor mount 54. Seal 57 and coupling 55 provide the connection between drive shaft 40 and motor 56. Extending from the back end of motor 56 is an electric cable 58 for connection to a power supply. A hand-held control mechanism or foot pedal mechanism may be used for regulating the speed of motor 56 and for optimizing the speed or rate of rotation of needle 12. For example, the speed of motor 56 may be increased so as to provide a very rapid rotation of needle 12 wherein the incremental advancement of needle 12 appears to approach a "continuous" rotation. Conversely, the motor speed may be reduced such that the incremental advancement of needle 12 is intermittent.

Stitcher 10 is also provided with a nose tip articulation means 51 which includes a handle or lever 46 (FIG. 5), two cables 50 each having a ball fitting 61 (FIG. 2), a cable anchor 52, a spring 44, and a brake shoe 48 (FIG. 6). Nose tip 20 is hinged and can be articulated about pivot point 49 at various angles, as shown in FIG. 6, by adjusting the position of handle or lever 46. Lever 46 is pivotally mounted at base 42 and is preferably located on stitcher 10 so as to be easily manipulated by the user's thumb or finger of the hand in which stitcher 10 is held. Lever 46 may be configured to be moveable along the length of the stitcher 10 for accommodating various surgical applications. Alternatively, the nose tip articulation mechanism of the present invention may include a low-profile finger tip lever or actuator located just proximal to head assembly 21.

Articulation means 51 further includes two cables 50 each extending substantially within and along the length of tubular body 30 from nose tip 20 to lever 46. Two ball fittings, one at the distal end of each cable 50, are held in respective sockets 61 located distally of the center of rotation or pivot point 49. The proximal ends of cables 50 are held by a cable anchor 52 mounted to lever 46. The cable anchor 52 provides the mechanism for adjusting the length of cables 50. Tension on cables 50 is provided by a spring 44 which is biased against a brake shoe 48 abutting the distal side of lever 46.

Thus, as shown in FIG. 6, clockwise pivoting of lever 46 causes the associated cable 50 to pull up on nose tip 20 and rotate it upward (designated in phantom at 70) about the center of rotation of point 49. Similarly, counter-clockwise pivoting of lever 46 causes the other associated cable 50 to pull upon on nose tip 20 and rotate it downward (designated in phantom at 71). Nose tip articulation means 51 allows nose tip 20 to be rotated within a total range of approximately 180°, more or less, or about 90°, more or less, left and right of a centered position. The force exerted by spring 44 maintains tension on cables 50 and applies a braking force on lever 46, and thus, serves to hold nose tip 20 in the selected articulated position.

The entire nose tip 20, including needle 12 and drive plate 16, may be pivoted while maintaining engagement between drive plate 16 and toggle 18. The spherical end of toggle 18, which engages drive plate 16, permits nose tip 20 to pivot and yet maintains the oscillating motion of drive plate 16 necessary to drive needle 12. By manually rotating stitcher 10 about its longitudinal axis and simultaneously articulating nose tip 20, the position of nose tip 20 and needle 12 therein can be varied to accommodate almost any suturing angle.

The way in which "C"-shaped needle 12 is engaged or held and advanced by drive plate 16 and toggle 18 combination, as disclosed, permits stitcher 10 to have a tip whose dimensions are not much larger than the width and height of needle 12 itself. The resulting small tip and profile of stitcher 10 provides good site access and visibility to the surgeon. Some or all of the distal portion of the stitcher 10 may comprise a removable cartridge containing at least needle 12 and attached thread 14 and which may be disposable.

It is further contemplated that the disclosed clutch mechanism may be utilized to engage, hold, and facilitate advancement of an arcuate needle by various other drive means, including drive means which provide continuous, rather than incremental, advancement of the arcuate needle.

Although stitcher 10 of the present invention has been described principally in conjunction with surgical suturing applications, it should be appreciated that it is not limited to surgical uses, and can also be used for any sewing or stitching application. Further, while embodiments and applications of this invention have been shown and described, it would be apparent to those skilled in the art that many other and further embodiments of the invention are possible without departing from the inventive concepts herein. The invention, therefore, is not to be restricted except in the spirit of the appended claims.

What is claimed is:

1. An automated stitching device, comprising:

an arcuate needle, drive means for converting rotary motion to oscillating motion to incrementally advance said arcuate needle in an arcuate path, and clutch means responsive to said drive means for releasably engaging and gripping said arcuate needle and incrementally advancing said arcuate needle in an arcuate path, wherein said clutch means comprises at least one static clutch body and at least one dynamic clutch body, and wherein said dynamic clutch body releasably engages and advances said arcuate needle responsive to said drive means, and said static clutch body releasably engages said needle to prevent movement of said needle in the arcuate path unless advanced by said dynamic clutch body.

2. The device of claim 1 wherein one or more of said clutch bodies further comprises multiple clutch finger means to releasably engage said arcuate needle.

3. An automated stitching device, comprising:

an arcuate needle, drive means for converting rotary motion to oscillating motion to incrementally advance said arcuate needle in an arcuate path, and clutch means responsive to said drive means for releasably engaging and gripping said arcuate needle and incrementally advancing said arcuate needle in an arcuate path, wherein said drive means comprises a crankshaft, toggle, and drive plate which convert rotary motion to oscillating motion to incrementally advance said arcuate needle, and further comprising means for articulating said arcuate needle while maintaining engagement between said toggle and said drive plate.

* * * * *